(12) United States Patent
Mautner et al.

(10) Patent No.: US 6,344,578 B1
(45) Date of Patent: Feb. 5, 2002

(54) PROCESS FOR WORKING UP RESIDUES FROM THE DIRECT SYNTHESIS OF ORGANOCHLOROSILANES

(75) Inventors: Konrad Mautner, Nünchritz; Bernd Köhler, Leckwitz; Gudrun Tamme, Boxdorf, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/915,038

(22) Filed: Jul. 25, 2001

(30) Foreign Application Priority Data

Aug. 10, 2000 (DE) .......................... 100 39 172

(51) Int. Cl.$^7$ .................................. C07F 7/08
(52) U.S. Cl. ................ 556/468; 556/467; 556/469
(58) Field of Search ................ 556/467, 468, 556/469

(56) References Cited

U.S. PATENT DOCUMENTS

| | | | |
|---|---|---|---|
| 2,681,355 A | | 6/1954 | Barry et al. |
| 4,130,632 A | | 12/1978 | Braunsperger et al. |
| 4,393,229 A | | 7/1983 | Ritzer et al. |
| 5,292,912 A | | 3/1994 | Chadwick et al. |
| 5,502,230 A | | 3/1996 | Mautner et al. |
| 5,627,298 A | * | 5/1997 | Freeburne et al. .......... 556/467 |
| 5,629,438 A | * | 5/1997 | Freeburne et al. ...... 556/467 X |
| 5,877,337 A | | 3/1999 | Mautner et al. |
| 5,907,050 A | * | 5/1999 | Crum et al. ................. 556/468 |
| 5,922,894 A | * | 7/1999 | Crum et al. ................. 556/468 |
| 6,013,235 A | * | 1/2000 | Brinson et al. ............. 556/468 |
| 6,271,407 B1 | * | 8/2001 | Colin et al. ................. 556/468 |

* cited by examiner

*Primary Examiner*—Paul F. Shaver
(74) *Attorney, Agent, or Firm*—Brooks & Kushman P.C.

(57) ABSTRACT

The invention relates to a process for preparing alkylchlorosilanes from the liquid constituents of the residues from the direct synthesis of alkylchlorosilanes which have a boiling point of above 70° C. at 1013 hPa and comprise disilanes, in which the residues are heated with hydrogen chloride and silicon at temperatures of at least 300° C., with at least 10% by weight of trichlorosilane and/or tetrachlorosilane, based on the weight of the alkylchlorosilanes formed, being formed at the same time.

11 Claims, No Drawings

PROCESS FOR WORKING UP RESIDUES FROM THE DIRECT SYNTHESIS OF ORGANOCHLOROSILANES

BACKGROUND OF THE INVENTION

1. Field of the Invention

The invention relates to a process for preparing alkylchlorosilanes from the liquid constituents of the residues from the direct synthesis of alkylchlorosilanes.

2. Background Art

In the direct synthesis of alkylchlorosilanes of the general formula $R_aH_bSiCl_{4-a-b}$ where a is 1–4 and b is 0, 1 or 2 from silicon metal and alkyl chlorides R—Cl, where R is methyl is particularly preferred, oligosilanes, carbosilanes, siloxanes and high-boiling decomposition products are formed as by-products. Furthermore, very fine solids from the direct synthesis which are not retained by cyclones and filters are also present in the distillation residue. The solids comprise silicon, metal chlorides, e.g. $AlCl_3$, metal silicides and carbon.

The predominant part of these residues constitute oligosilanes, in particular the disilanes $R_cCl_{6-c}Si_2$, where c is 0–6. For this reason, processes which convert the disilanes into monosilanes have been developed. Conversion may be achieved, for example, by amine-catalyzed cleavage with hydrogen chloride. However, only disilanes having fewer than 4 methyl groups can be cleaved by this process. Furthermore, the disilanes must be separated beforehand from the solid residues, since these residues, for example aluminum chloride, act as catalyst poisons.

In order to also recycle uncleavable disilanes, processes in which uncleavable disilanes are converted into cleavable disilanes and then cleaved, e.g. as described in U.S. Pat. No. 4,393,229, or in which these disilanes are cleaved directly by means of HCl over specific catalysts, usually comprising noble metals, e.g. as described in U.S. Pat. No. 5,502,230, have been developed. A disadvantage of metal-catalyzed reactions is always the tendency for the catalysts to be poisoned by impurities from the residue.

U.S. Pat. No. 2,681,355 describes a process in which relatively high-boiling residues from the direct synthesis of methylchlorosilanes are converted into monomeric silanes purely thermally, in the absence of catalysts, by employing hydrogen chloride at temperatures of 400–900° C. in an autoclave or in a tubular reactor. The patent emphasizes the low tendency to form carbon deposits as a great advantage when using a tubular reactor, as a result of which the process is said to be operable for a prolonged period. However, this does not apply when treating residues which, because of their solids content, quickly lead to blockage of reaction tubes.

U.S. Pat. No. 5,877,337 describes a process which allows even solids-containing residues from the direct synthesis of organochlorosilanes to be worked up at low pressures and yet allows the organosilicon components to be converted into useful silanes. This objective is achieved by thermal cleavage of the direct synthesis residues with hydrogen chloride at temperatures of 300–800° C. in a tubular reactor having rotating internals. The rotary motion of the internals strips off caked deposits on the reactor walls caused by carbonization or by deposition of solid components, thus preventing blockage of the reactor. However, this process is technically difficult to implement and is therefore correspondingly costly.

U.S. Pat. No. 5,592,912 describes a process for the cleavage of direct synthesis high-boiling residue with HCl in the presence of catalysts such as activated carbon, or supported aluminum chloride, platinum, or palladium compounds. Supports described are aluminum oxide, silica, zeolites and active carbon. The process can be carried out as a fixed-bed process or in a fluidized bed.

The preparation of trichlorosilane and tetrachlorosilane mixtures from silicon and hydrogen chloride in a fluidized bed has been described, for example, in U.S. Pat. No. 4,130,632.

The processes mentioned above suffer from the disadvantage of a high outlay in terms of apparatus required to solve the carbonization problem or the use of specific catalysts, sometimes based on noble metals, which make the process more expensive.

SUMMARY OF THE INVENTION

It is an object of the invention to provide an improved process which allows work up of solids-containing residues from the direct synthesis of alkylchlorosilanes, and which allows the organosilicon components to be converted into usable silanes.

DETAILED DESCRIPTION OF THE PREFERRED EMBODIMENT(S)

The invention provides a process for preparing alkylchlorosilanes from the liquid constituents of the residues from the direct synthesis of alkylchlorosilanes which have a boiling point above 70° C. at 1013 hPa and comprise disilanes, in which the residues are heated with hydrogen chloride and silicon at temperatures of at least 300° C., wherein at least 10% by weight of trichlorosilane and/or tetrachlorosilane, based on the weight of the alkylchlorosilanes formed, are formed concurrently. The process is, in particular, simple to carry out, and allows very long running times.

Hydrogen chloride and Si metal react in an exothermic reaction to produce a mixture of trichlorosilane and tetrachlorosilane. The equilibrium composition of the mixture is dependent on the reaction temperature. The reaction enthalpy is utilized to heat the liquid constituents of the residues from the direct synthesis of alkylchlorosilanes fed into the reactor to reaction temperatures at which the cleavage by means of hydrogen chloride to form monosilanes then takes place. In the process, it is preferred that at least 20% by weight, in particular at least 30% by weight, of trichlorosilane and/or tetrachlorosilane, based on the weight of the alkylchlorosilanes formed, are formed at the same time. The product obtained is a mixture of trichlorosilane and tetrachlorosilane together with varying proportions of organochlorosilanes, depending on the composition of the liquid constituents of the residues. The silicon is preferably present as a fixed bed or, in particular, in a fluidized bed in the process.

The amount of HCl can be varied within a wide range and, in the case of fluidized-bed reactors, the lower limit is determined essentially by the minimum amount required for maintaining the fluidized bed, while the upper limit is determined essentially by the need to avoid excessive discharge of dust from the fluidized bed. Both are highly dependent on the particle size and the geometry of the reactor. In fixed-bed reactors, the amount of HCl is limited by plant engineering considerations and economic constraints, e.g. by the loss of HCl. The amount of hydrogen chloride used is at least the molar equivalent amount of the disilanes present in the residue and the trichlorosilanes and/or tetrachlorosilanes to be formed. The residue and the hydrogen chloride may both be preheated, or may be metered at ambient temperature into the reactor, with the streams preferably being metered in continuously. When heating is utilized, the residue can also be metered in as a gas/liquid mixture. Preference is given to using a fluidized-bed reactor. Preference is further given to using customary plants for the preparation of trichlorosilane and tetrachlorosilane.

The alkylchlorosilanes prepared by cleavage of disilanes from the liquid constituents of the residues from the direct synthesis of alkylchlorosilanes preferably have the above general formula where R is a methyl, ethyl, butyl or propyl radical, in particular a methyl radical. Most preferably, methyltrichlorosilane, dimethylchlorosilane, trimethylchlorosilane, methyldichlorosilane, or dimethylchlorosilane are prepared.

The target product of the direct synthesis of methylchlorosilanes is generally dimethyldichlorosilane which has a boiling point of 70° C. and usually makes up more than 80% of the crude mixture and is purified by distillation. The residues from the direct synthesis having a boiling point above 70° C., preferably at least 80° C., in particular at least 100° C., comprise, inter alia, monosilanes, e.g. ethyldichlorosilane, ethylmethyldichlorosilane, ethyltrichlorosilane or i-propyltrichlorosilane. The proportions can fluctuate greatly and are usually less than 10% of the residue. Greatly fluctuating proportions of disilanes, e.g. hexamethyldisilane, pentamethylchlorodisilane, 1, 1 -dichloro-1,2,2,2-tetramethyldisilane, 1 ,2-dichloro- 1,1,2,2-tetramethyldisilane, 1,1,2-trichloro-1,2,2-trimethyldisilane, 1,1,1-trichloro-2,2,2-trimethyldisilane, 1,1,1,2-tetrachloro-2,2-dimethyldisilane, 1,1 ,2,2-tetrachloro-1,2-dimethyldisilane, pentachloromethyldisilane and hexachlorodisilane, make up the major part of the residue. The proportion of disilanes is usually 20–80%, most often 40–80% of the residue. Further constituents are carbosilanes, oligosilanes having three or more silicon atoms, hydrocarbons, and chlorinated hydrocarbons whose identification and quantification present great difficulties.

In addition, the proportion of solids can be up to 10% by weight. These include finely divided or very finely divided solids, for example, silicon and suicides, generally contaminated with catalyst and promoter residues, metal chloride mixtures comprising main constituents such as $AlCl_3$, $CaCl_2$, CuCl, and also including carbon. A detailed description of the residues is given, for example, in U.S. Pat. No. 5,292,912. The process is preferably carried out in the presence of the solids, since these do not adversely affect the process.

The silicon can be used in milled form or in lump or granular form. It is preferably used in excess for the preparation of trichlorosilane and/or tetrachlorosilane. It is preferable for further silicon to be fed in continuously.

The amount of liquid constituents of the residues from the direct synthesis of alkylchlorosilanes which is fed to the reaction depends on the need to maintain both the necessary temperature in the reactor, or the fluidized bed, if the latter is used.

The mixture obtained in the reaction and leaving the reactor is condensed, if appropriate freed of solids, and may be returned in whole or in part to the silane mixture produced in the direct synthesis, or may be fractionated separately into pure substances.

The components of the residue which are not cleavable under the conditions of the process, e.g. metal salts and other solids, generally deposit on the silicon surfaces and are finally discharged together with very finely divided silicon in the reaction gas, from which they are separated by means of devices such as filters or cyclones. However, the uncleavable components may also remain in the reactor, from which they may then periodically be discharged, together with the residual contents of the reactor. The solids in both cases can, after suitable treatment, be used as additives in the ceramics industry or as slag formers. If the metal content is sufficiently high, it may also be worthwhile to isolate these metals from the solids; for example, copper can be leached out and returned to the materials circuit.

The process is preferably carried out at temperatures of at least 400° C., preferably at least 450° C., and not more than 1200° C. At temperatures higher than 600° C. in the reactor, elimination of silicon-bound alkyl groups begins to occur in competition to the cleavage, resulting in formation of chlorodisilanes, and chlorosilanes such as trichlorosilane or tetrachlorosilane. This reaction can be exploited to keep the cost of distillation for fractionating the product mixture low. However, preference is given to obtaining the alkylchlorosilanes in admixture with trichlorosilane and tetrachlorosilane, and using the alkylchlorosilanes obtained after purification by distillation for preparing silicone products such as polydimethylsiloxane or silicone resins.

The pressures prevailing in the reactor during the process can be varied within a wide range and are preferably in the range of 1–5 bar (abs.). Particular preference is given to operating the reactor fully continuously, with both the residues and the silicon being added continuously. If desired, a plurality of introduction points for a given stream, e.g. residues or HCl, can be provided along the length of the reactor.

In the following examples, unless indicated otherwise, all percentages are by weight; all pressure are 1013 hPa (atmospheric pressure); and all temperatures are 20° C.

EXAMPLES

Comparative Example Cl (based on U.S. Pat. No. 2,681,355, not according to the invention)

180 ml/h of high-boiling residue from the silane synthesis having a boiling point of greater than 150° C. and 25 l/h of gaseous hydrogen chloride were fed concurrently at room temperature and ambient pressure into a laboratory reactor (hollow tube) which had a length of 700 mm and an internal diameter of 25 mm, with provision for electrical heating, set to a temperature of 300° C. The high-boiling residue consisted of 80% of disilanes, a mixture of 1,1,2,2-tetrachlorodimethyldisilane, 1, 1,2-trichlorotrimethyldisilane and 1,2-dichlorotetramethyldisilane, 2% of solids and 18% of siloxanes and carbosilanes. A more precise compositional assignment was difficult because of the large number of by-products. After 17 hours of operation, the experiment was stopped since the tube reactor had become blocked by solids and decomposition products in the reaction zone. During the experiment, a silane cleavage product having the composition set forth in Table 1 was obtained:

TABLE 1

| Components | Proportion in Silane Cleavage Product [% by weight] | |
| --- | --- | --- |
| | Comparative Example C1 | Example 1 |
| Dimethylchlorosilane | 1 | 0* |
| Methyldichlorosilane | 10 | 7 |
| Trimethylchlorosilane | 2 | 1 |
| Methyltrichlorosilane | 35 | 25 |
| Dimethyldichlorosilane | 32 | 12 |
| Solids | 3 | 0 |
| Others | 17 | 55 |

*All values are the proportion of the component in the silane cleavage product in percent by weight.

Example 1
(According to the Invention)

70 ml/h of high-boiling residue from the silane synthesis having a boiling point of greater than 150° C. and 25 l/h of gaseous hydrogen chloride were fed concurrently at room temperature and ambient pressure into an electrically heated laboratory fluidized-bed reactor having a length of 500 mm and an internal diameter of 40 mm, filled with 266 g of silicon, d(0.5): 70–80 μm. The temperature was set to 600° C. The high-boiling residue comprised 75 % of disilanes, a mixture of tetrachlorodimethyldisilane, trichlorotrimethyldisilane, dichlorotetramethyldisilane and other silanes. A more precise assignment was difficult because of the large number of by-products. After 20 hours of operation, the experiment was stopped without deposits having been formed. About 100 g/h of silane mixture comprising, as main constituents, about 20 % of trichlorosilane and about 40% of silicon tetrachloride was formed. After separation of the trichlorosilane and silicon tetrachloride, a silane cleavage product having the composition set forth in Table 1 was obtained during the experiment.

What is claimed is:

1. A process for preparing alkylchlorosilanes from disilane-containing liquid residue from the direct synthesis of alkylchlorosilanes, said residue having a boiling point above 70° C. at 1013 hPa, said process comprising:

heating the residues with hydrogen chloride and silicon metal in a reactor at temperatures of at least 300° C., such that at least 10% by weight of trichlorosilane and/or tetrachlorosilane, based on the total weight of the alkylchlorosilanes formed, are also formed.

2. The process of claim 1, wherein the silicon is present in a fluidized bed reactor.

3. The process of claim 1, wherein the temperature is at least 400° C.

4. The process of claim 2, wherein the temperature is at least 400° C.

5. The process of claim 1, wherein both the residues and the silicon are added continuously to the reactor.

6. The process of claim 2, wherein both the residues and the silicon are added continuously to the reactor.

7. The process of claim 3, wherein both the residues and the silicon are added continuously to the reactor.

8. The process of claim 4, wherein both the residues and the silicon are added continuously to the reactor.

9. The process of claim 1, wherein said residue further comprises finely divided solids from the direct synthesis.

10. The process of claim 1, wherein the residues have a boiling point of 80° C. or higher.

11. The process of claim 1, wherein the residues have a boiling point of 100° C. or higher.

* * * * *